(12) United States Patent
Patterson et al.

(10) Patent No.: US 10,945,871 B2
(45) Date of Patent: Mar. 16, 2021

(54) ORTHOTIC LEG SUPPORT APPARATUS

(71) Applicants: William Stanley Patterson, Orlando, FL (US); Michael Eden Littles, Orlando, FL (US)

(72) Inventors: William Stanley Patterson, Orlando, FL (US); Michael Eden Littles, Orlando, FL (US)

( * ) Notice: Subject to any disclaimer, the term of this patent is extended or adjusted under 35 U.S.C. 154(b) by 0 days.

(21) Appl. No.: 16/598,867

(22) Filed: Oct. 10, 2019

(65) Prior Publication Data

US 2020/0113723 A1 Apr. 16, 2020

Related U.S. Application Data

(60) Provisional application No. 62/743,834, filed on Oct. 10, 2018.

(51) Int. Cl.
*A61F 5/05* (2006.01)
*A61F 5/01* (2006.01)

(52) U.S. Cl.
CPC .......... *A61F 5/0113* (2013.01); *A61F 5/0127* (2013.01)

(58) Field of Classification Search
CPC ........ A61F 5/0113; A61F 5/0127; A61F 5/14; A61F 5/0111; A43B 7/147; A43B 7/20; A43B 7/22; A43B 7/226; A43B 13/12; A43B 13/125; A43B 13/127
USPC ................ 36/89, 107–110; 128/882; 602/23, 602/27–29, 62, 65–66
See application file for complete search history.

(56) References Cited

U.S. PATENT DOCUMENTS

| | | | |
|---|---|---|---|
| 3,827,430 A | 8/1974 | Fadden | |
| 4,289,122 A | 9/1981 | Mason et al. | |
| 5,088,479 A | 2/1992 | Detoro | |
| 5,352,189 A * | 10/1994 | Schumann | A61F 5/0111 602/23 |
| 5,431,624 A * | 7/1995 | Saxton | A61F 5/0127 36/89 |
| 5,961,477 A | 10/1999 | Turtzo | |
| 6,056,712 A * | 5/2000 | Grim | A61F 5/0127 602/16 |
| 6,319,218 B1 | 11/2001 | Birmingham | |
| 6,423,021 B1 * | 7/2002 | Gallegos | A61F 5/0111 602/23 |
| 7,077,818 B2 | 7/2006 | Ingimundarson et al. | |
| 7,112,180 B2 | 9/2006 | Guenther | |
| 7,112,181 B1 * | 9/2006 | DeToro | A61F 5/0127 602/27 |

(Continued)

*Primary Examiner* — Ophelia A Hawthorne
*Assistant Examiner* — Camtu T Nguyen
(74) *Attorney, Agent, or Firm* — Christopher M. Ramsey; GrayRobinson, P.A.

(57) ABSTRACT

An orthotic apparatus includes a leg securing member adapted for attachment to a wearer's lower leg. A resilient strut that flexes in the anterior to posterior direction has an upper end connected to the leg securing member. A heel member is connected to the strut lower end at the heel member. A foot member is connected to the heel member. The foot member has a heel end at the heel member and a toe end spaced horizontally from the heel end. The foot member also has a substantially rigid lower foot plate extending between the heel end and toe end and a substantially rigid upper foot plate extending between the heel end and toe end above and generally parallel to the lower foot plate. In certain examples the orthotic apparatus is integrated with a shoe.

63 Claims, 10 Drawing Sheets

(56) References Cited

U.S. PATENT DOCUMENTS

| | | |
|---|---|---|
| 7,125,392 B2 | 10/2006 | Scott |
| 7,270,644 B2 | 9/2007 | Ingimundarson |
| 7,513,880 B2 | 4/2009 | Ingimundarson et al. |
| 7,740,602 B2 | 6/2010 | Christensen |
| 8,465,445 B2 | 6/2013 | George |
| 8,904,674 B2 | 12/2014 | Schwartz |
| 9,504,592 B2 * | 11/2016 | Schwartz ................. A43B 7/20 |
| 2005/0054963 A1 | 3/2005 | Ingimundarson |
| 2010/0101118 A1 | 4/2010 | Guenther |
| 2015/0216703 A1 * | 8/2015 | Madden ................. A61F 5/0127 602/7 |

* cited by examiner

ORTHOTIC LEG SUPPORT APPARATUS

CROSS-REFERENCE TO RELATED APPLICATION

This claims the benefit of priority from provisional Application No. 62/743,834, filed Oct. 10, 2018, which is incorporated by reference in its entirety.

FIELD

This pertains to the field of leg braces and, more particularly, to orthotic leg supports.

BACKGROUND

Many people with back, hip, or leg injuries live with chronic pain that impacts their lives and limits their physical activity. Devices such as ankle foot orthotic braces or "AFOs" have been developed to help assist with their mobility, but conventional AFOs are typically designed to deal with foot and ankle problems only. They are not generally designed to alleviate back pain or hip pain caused by daily activities and they are often too rigid to allow the wearer to comfortably traverse stairs or operate an automobile gas pedal.

BRIEF SUMMARY

An improved orthotic apparatus that overcomes these drawbacks includes an orthotic apparatus having an anterior and posterior. The orthotic apparatus includes: a leg securing member adapted for attachment to a wearer's lower leg and a resilient strut that flexes in the anterior to posterior direction. The strut has a strut upper end and a strut lower end, the strut upper end being connected to the leg securing member. A heel member is connected to the strut lower end. And a foot member is connected to the heel member. The foot member has a heel end at the heel member and a toe end spaced horizontally from the heel end. The foot member includes (a) a substantially rigid lower foot plate extending between the heel end and toe end and (b) a substantially rigid upper foot plate extending between the heel end and toe end above and generally parallel to the lower foot plate.

Implementations of the orthotic apparatus may include one or more of the following features.

The orthotic apparatus may include a shoe, where the lower foot plate is positioned within a sole of the shoe and the upper foot plate is positioned on a foot bed of the shoe.

The strut, upper foot plate, and lower foot plate may be composed of resilient fiber-reinforced composite material.

The lower foot plate and heel member may be monolithic and the upper foot plate may be connected to the lower foot plate by a rigid mechanical link between the upper foot plate and lower foot plate.

In some examples, the upper foot plate is not in direct contact with the heel member.

The heel member may be substantially cup-shaped and includes a recessed region that allows the heel member to flex in the anterior to posterior direction.

The upper foot plate may be a flattened plate emulating a silhouette of wearer's foot in such a way that a bottom of the wearer's foot can rest completely on the upper foot plate. The lower foot plate may be a flattened plate extending from the heel end towards the toe end at least the same distance as the upper foot plate. The upper foot plate may be connected to the lower foot plate by a plurality of rigid mechanical links between the upper foot plate and lower foot plate where a first of the rigid mechanical links is towards the heel end and a second of the rigid mechanical links being towards the toe end. The rigid mechanical links extend vertically from the lower foot plate to the upper foot plate.

Another example of the orthotic apparatus includes a shoe having a shoe heel end, a shoe toe end, and a sole. The orthotic apparatus also includes a foot member having a lower foot plate within the sole and an upper foot plate forming a foot bed of the shoe, the lower foot plate and upper foot plate extending from the shoe heel end toward the shoe toe end. A heel member at the shoe heel end is connected to the lower foot plate. A lower end of a resilient strut is connected at the heel member and extending vertically. A leg securing member for securing to a wearer's lower leg is connected to an upper end of the strut.

Implementations of this orthotic apparatus may include one or more of the following features.

The strut, upper foot plate, and lower foot plate may be composed of resilient fiber-reinforced composite material.

The lower foot plate and heel member may be monolithic and the upper foot plate may be connected to the lower foot plate by a rigid mechanical link between the upper foot plate and lower foot plate.

In some examples, the upper foot plate may not be in direct contact with the heel member.

The heel member may be substantially cup-shaped and may include a recessed surface that allows the heel member to flex in the anterior to posterior direction, thereby permitting plantar flexion and dorsiflexion of the foot member.

The upper foot plate may be a flattened plate emulating a silhouette of wearer's foot in such a way that a bottom of the wearer's foot can rest completely on the upper foot plate where the lower foot plate is a flattened plate extending from the shoe heel end towards the shoe toe end at least the same distance as the upper foot plate. The upper foot plate may be connected to the lower foot plate by a plurality of rigid mechanical links between the upper foot plate and lower foot plate. A first of the rigid mechanical links is towards the shoe heel end and a second of the rigid mechanical links is towards the shoe toe end. The rigid mechanical links extend vertically from the lower foot plate to the upper foot plate through the sole.

An example of a method of treating back and/or hip pain while walking includes wearing the orthotic apparatus by attaching the leg securing member to the wearer's lower leg beneath the knee and resting the wearer's foot atop the upper foot plate while the wearer walks.

Implementations of method may include one or more of the following features.

The method may also include a shoe, where the lower foot plate is positioned within a sole of the shoe and the upper foot plate is positioned on a foot bed of the shoe.

The strut, upper foot plate, and lower foot plate may be composed of resilient fiber-reinforced composite material.

The lower foot plate and heel member may be monolithic and the upper foot plate may be connected to the lower foot plate by rigid mechanical link between the upper foot plate and lower foot plate.

In some examples, the upper foot plate may not be in direct contact with the heel member.

The heel member may be substantially cup-shaped and may include a recessed region that allows the heel member to flex in the anterior to posterior direction.

The upper foot plate may be a flattened plate emulating a silhouette of wearer's foot in such a way that a bottom of the wearer's foot can rest completely on the upper foot plate. The lower foot plate may be a flattened plate extending from the heel end towards the toe end at least the same distance as the upper foot plate. The upper foot plate may be connected to the lower foot plate by a plurality of rigid mechanical links between the upper foot plate and lower foot plate. A first of the rigid mechanical links is towards the heel end and a second of the rigid mechanical links is towards the toe end. The rigid mechanical links extend vertically from the lower foot plate to the upper foot plate.

The apparatus is adapted to improve the wearer's mobility by allowing the wearer to have a natural gait, heel strike, and toe off during a step. It further allows for ankle plantar flexion and dorsiflexion, which allows the wearer to drive a car and/or walk up and down stairs comfortably.

DETAILED DESCRIPTION OF EXAMPLE EMBODIMENTS

Figure 1:
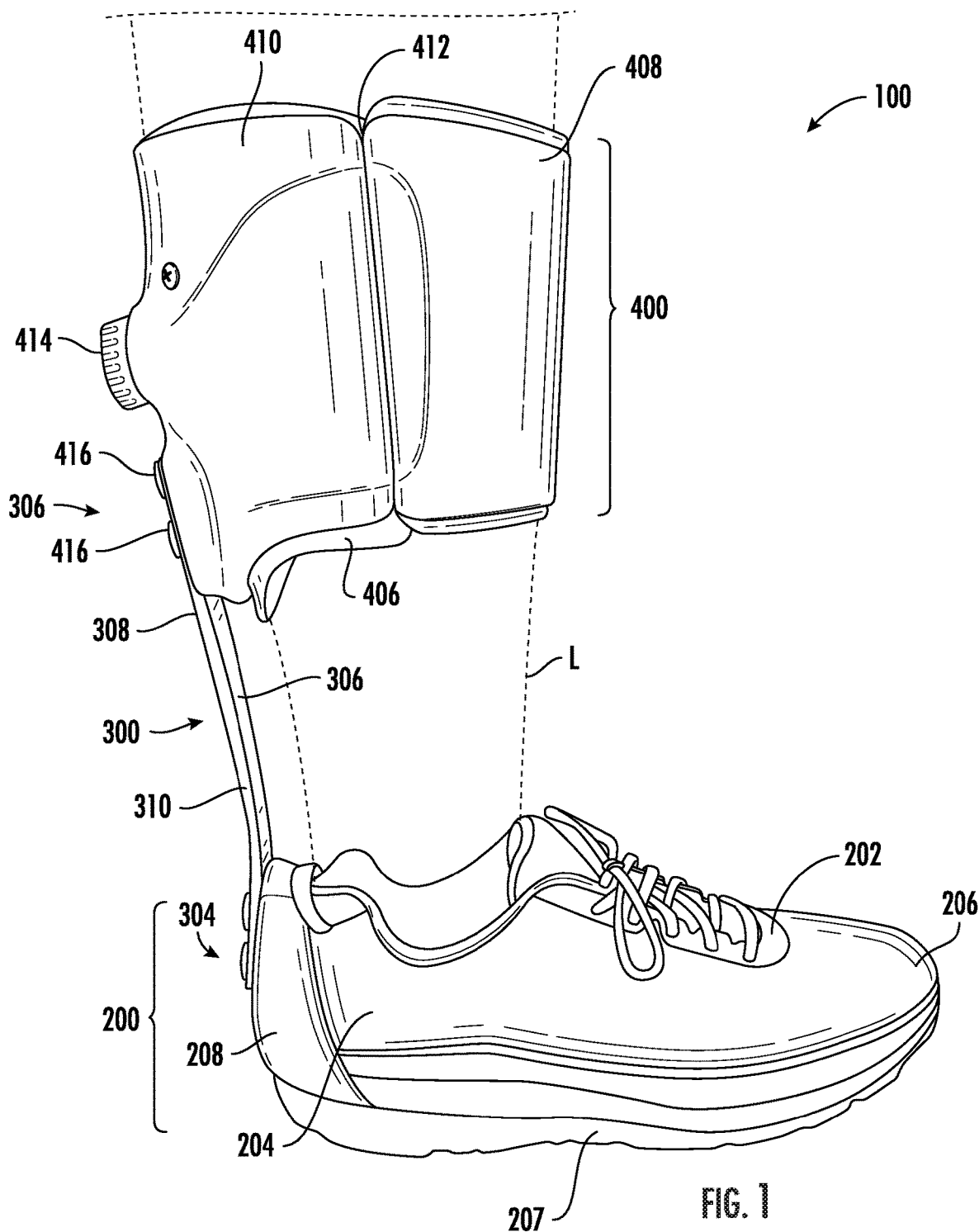
FIG. 1 is a lateral side perspective view of an example of the orthotic apparatus.
Figure 2:
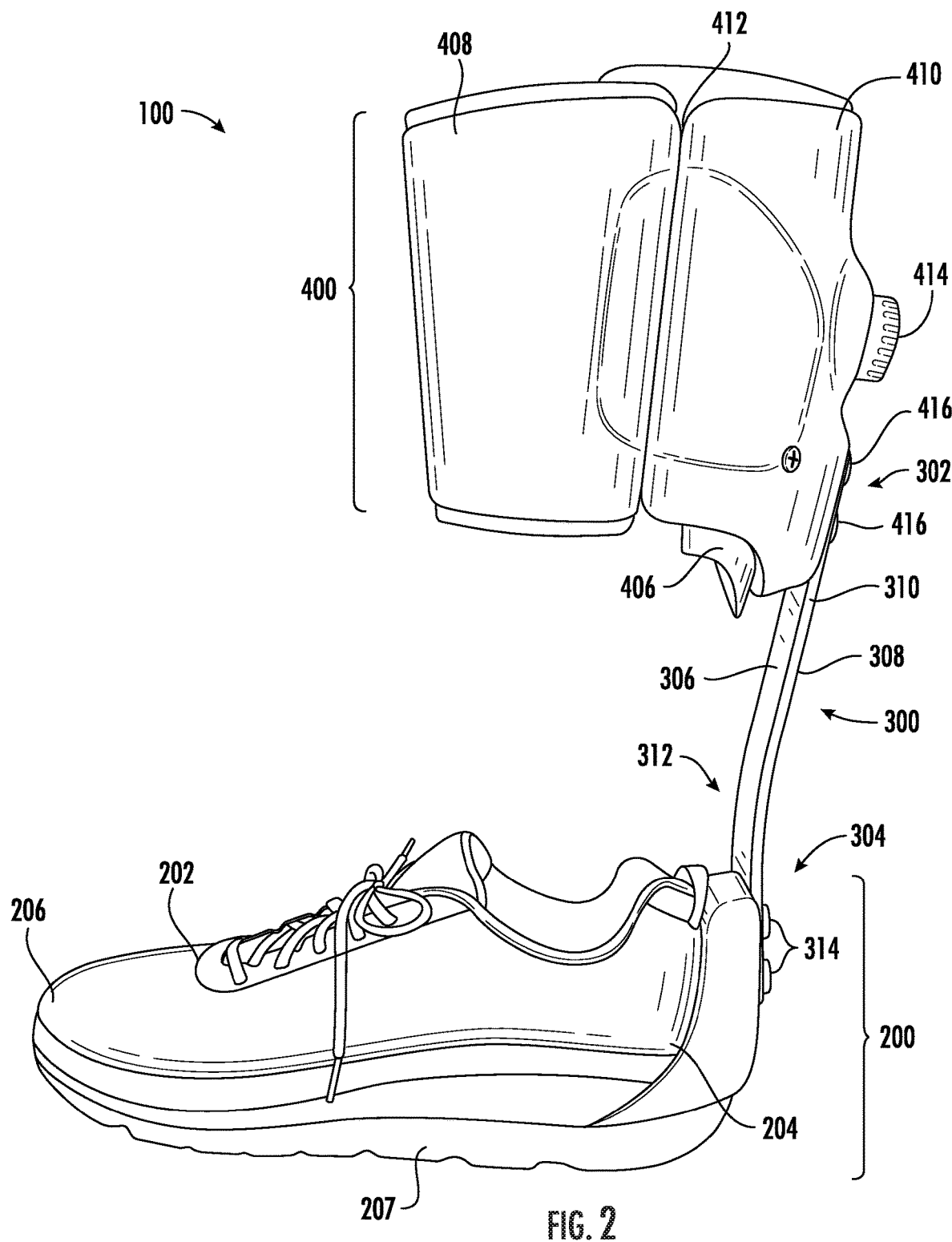
FIG. 2 is a medial side perspective view thereof.
Figure 3:
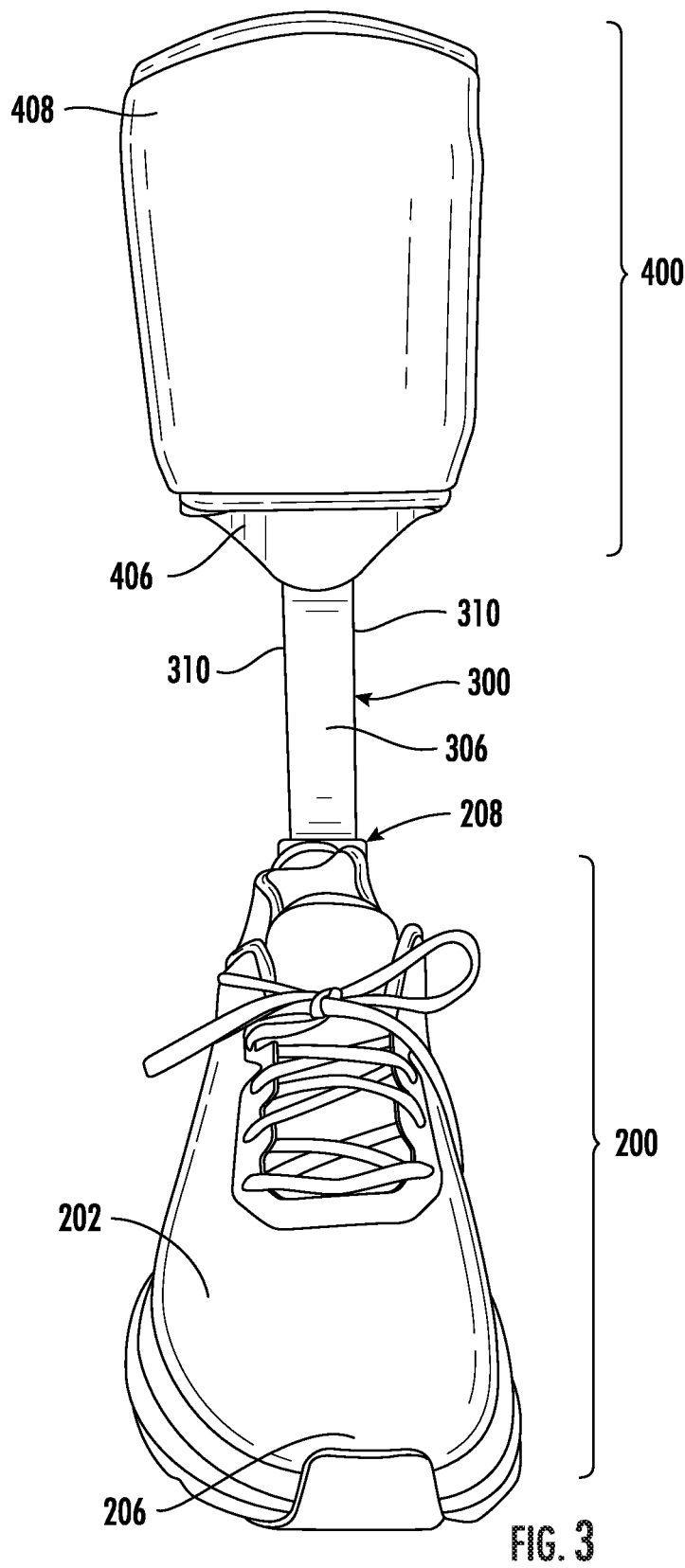
FIG. 3 is an anterior perspective view thereof.
Figure 4:
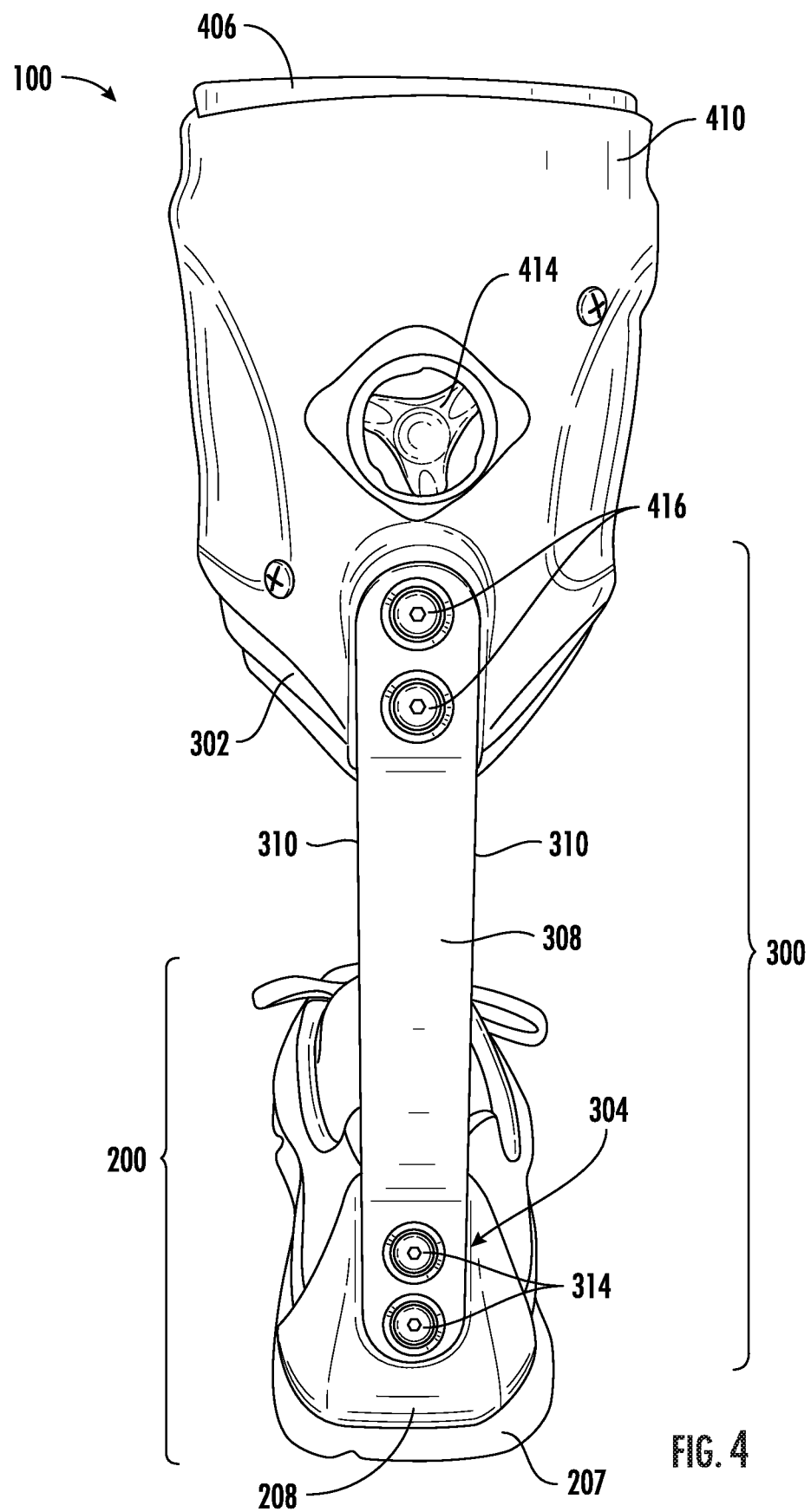
FIG. 4 is a posterior perspective view thereof.
Figure 5:
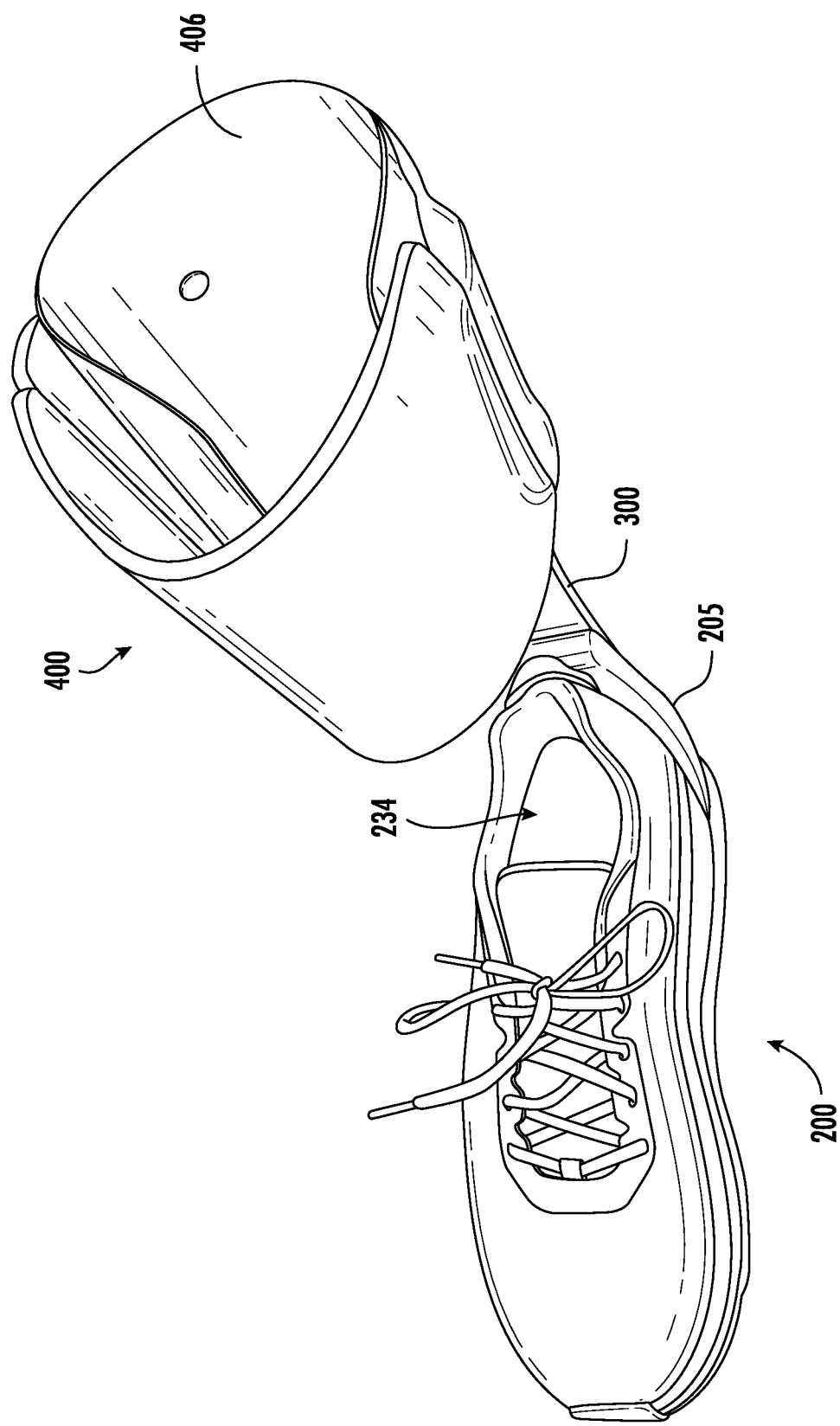
FIG. 5 is a top perspective view thereof.

This disclosure describes exemplary embodiments, but not all possible embodiments of the orthotic apparatus. Where a particular feature is disclosed in the context of a particular example, that feature can also be used, to the extent possible, in combination with and/or in the context of other examples. The orthotic apparatus may be embodied in many different forms and should not be construed as limited to only the examples described here.

Referring to FIGS. 1-5, an example of the orthotic apparatus 100 includes a foot member 200, a strut 300, and a leg securing member 400. These components work together to support the lower leg L of the wearer by distributing forces against the wearer's foot from the foot member 200, through the strut 300, and to the leg securing member 400. The orthotic apparatus 100 allows the wearer to maintain a natural gait by permitting plantar flexion and dorsiflexion of the foot about the wearer's ankle. By allowing the wearer maintain a natural gait, the wearer may achieve pain relief from conditions causing leg pain, hip pain, and/or back pain, for example.

The leg securing member 400 is adapted to be attached to the wearer's lower leg L below the knee in such a way that the leg securing member 400 distributes forces travelling up the strut 300 into the wearer's lower leg L. The leg securing member 400 may have many different forms. It may circumscribe the leg L as shown in the drawings or it may only partially circumscribe the leg and be secured with one or more straps or the like. The form of the leg securing member 400 is not critical so long as it is capable of distributing the forces travelling up the strut 300 into the wearer's lower leg L.

In the example shown, the leg securing member 400 includes a sleeve 402 defining an interior portion 404 shaped to fit snugly around the lower leg L and mimic the outline of the lower leg L. The sleeve 402 may include an insert 406 that provides a smooth surface for contacting the leg L to prevent discomfort.

The sleeve 402 further includes an anterior section 408 and a posterior section 410 that are separable about a seam 412 by adjusting an actuator 414. By loosening the actuator 414, the anterior section 408 and a posterior section 410 separate and vice versa. This construction allows the inner diameter of the sleeve 402 to be increased or decreased to accommodate different sized legs and for installation on the leg. It also allows the sleeve 402 to be fitted tightly to the leg L to ensure the forces from the strut 300 are distributed into the lower leg L.

The leg securing member 400 may be connected to the strut 300 on the posterior of the leg securing member 400 with a connecting mechanism such as the one shown. In the example shown, the connecting mechanism includes at least one threaded fastener 416 or the like. In other examples the strut 300 and leg securing member 400 may be connected by being integrally formed together.

The leg securing member 400 may be made primarily of metal, plastic, or composite depending on the wearer's medical condition. In one particular example, it is made of a rigid resilient material such as a plastic or fabric reinforced polymer composite material such as carbon fiber or the like. Constructing the leg securing member 400 out of a rigid resilient material allows the leg securing member 400 to flex enough to form a tight fit to the leg L but also distribute the forces from the strut 300.

The strut 300 is positioned on the posterior of the leg L when worn and attaches at its upper end 302 to the leg securing member and at its lower end 304 to the foot member 200. The strut 300 is constructed of a rigid but resilient material that allows it to flex slightly in the anterior to posterior direction but not substantially flex in the medial to lateral direction. Such a rigid but resilient material maybe plastic or fabric reinforced polymer composite material such as carbon fiber or the like.

Although this construction is not necessary in every case, the strut 300 in the example shown includes an anterior side 306, a posterior side 308, and opposed sidewalls 310. The anterior side 306 and posterior side 308 extend vertically in a substantially parallel manner and have a lateral width greater than the longitudinal thickness of the strut 300. The longitudinal thickness is defined by the longitudinal length of the sidewalls 310.

Proximal to the foot member 200, the strut 300 includes a curved section 312 that forms a bend in the strut in the anterior to posterior direction. The bend allows the strut to more closely mimic the shape of the posterior portion of the wearer's leg L and to allow the strut 300 to be connected to the heel member 208 in a generally vertical orientation. The strut 300 is connected at it's the lower end 304 to the foot member 200 with at least one threaded fastener 314 or the like.

Additional details of the foot member 200 are now described with reference to FIGS. 6-11 as well as FIGS. 1-5. The foot member 200 may include an article of footwear 202. As used herein, the term "shoe" is used to refer generally to an article of footwear that falls into the general class of shoes, including footwear such as shoes themselves, boots, sandals, and the like. The shoe 202 includes a heel 204, a toe 206, a sole 207, and a foot bed 234. The foot bed 234 is the interior bottom of the shoe 202 on which the wearer's foot rests when worn. It should be understood that a shoe may not be necessary in every example of the foot member 200. The foot bed 234 may include a layer of padding for comfort.

Figure 7:
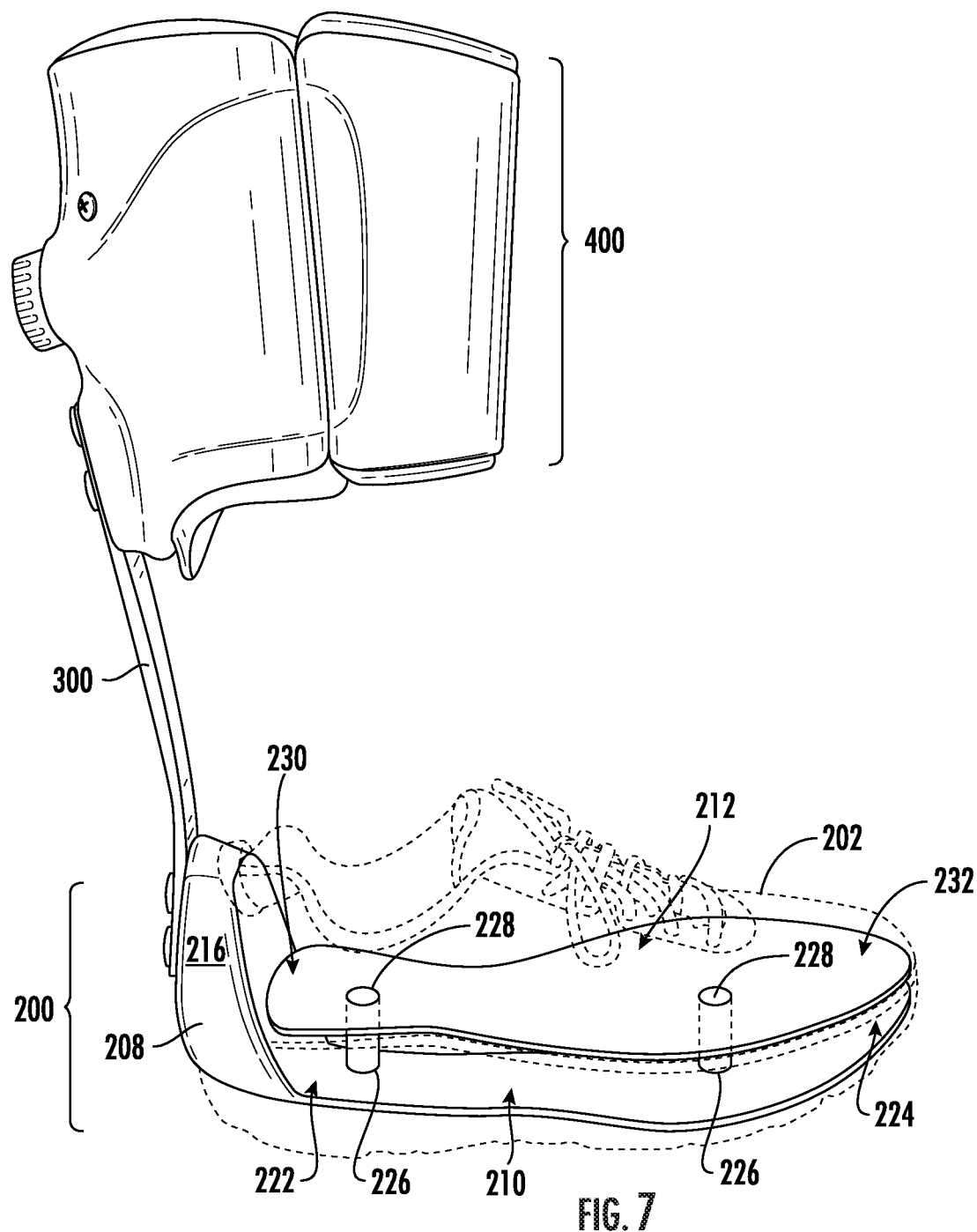
FIG. 7 is the same view as FIG. 1 with the shoe shown in dashed lines so that the orthotic apparatus is visible within the shoe.
Figure 8:
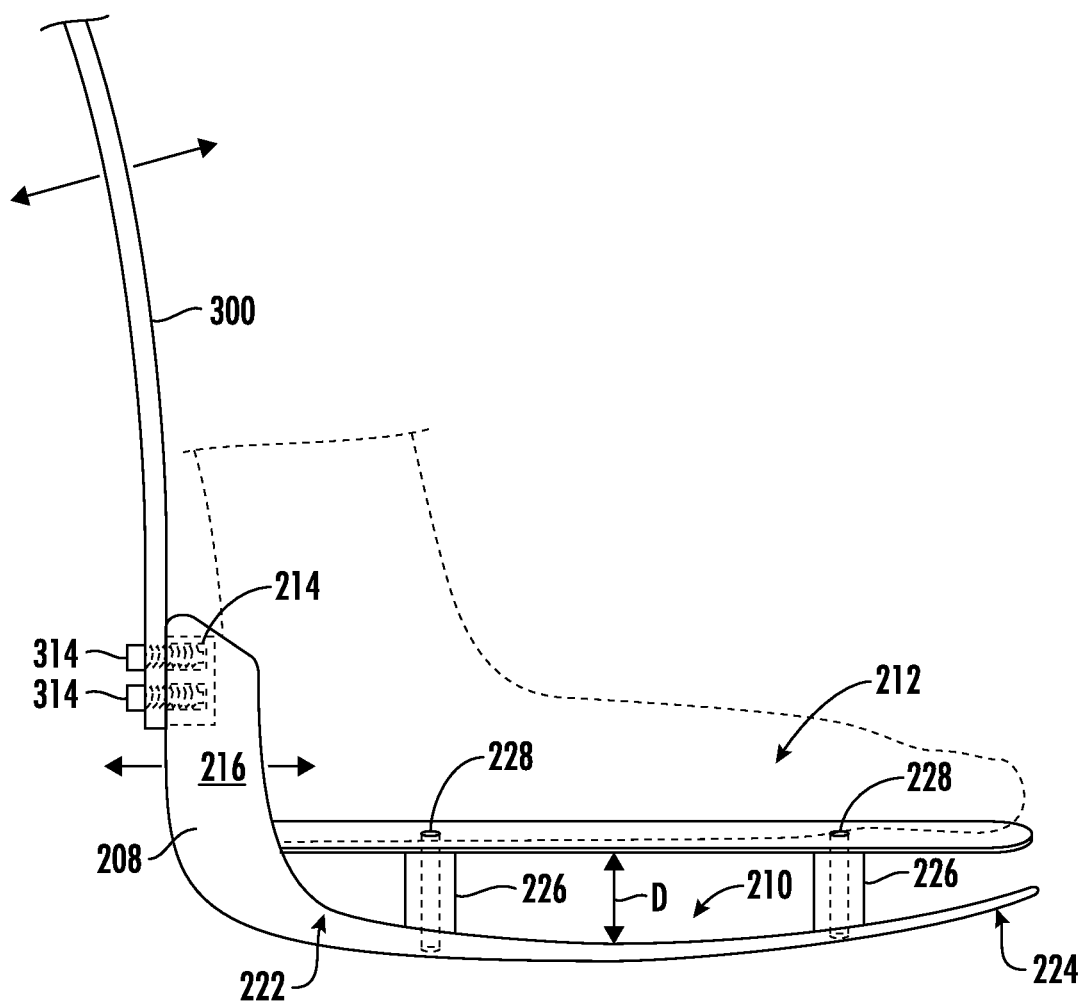
FIG. 8 is a side view of the orthotic apparatus apart from the shoe.

Referring now to FIGS. 7 and 8 in particular, details of the foot member apart from the shoe 202 are described. The foot member 200 includes a heel member 208, a lower foot plate 210, and an upper foot plate 212.

The heel member 208 may be connected to the strut 300 using the threaded fasteners 314 with a connection point 214 that mates with the threaded fasteners 314. The connection point 214 may be made of metal or another strong and rigid material. For added strength, the connection point 214 may be molded directly into the heel member material. In other examples, the heel member 208 and strut 300 are connected by being integrally formed together.

Figure 9:
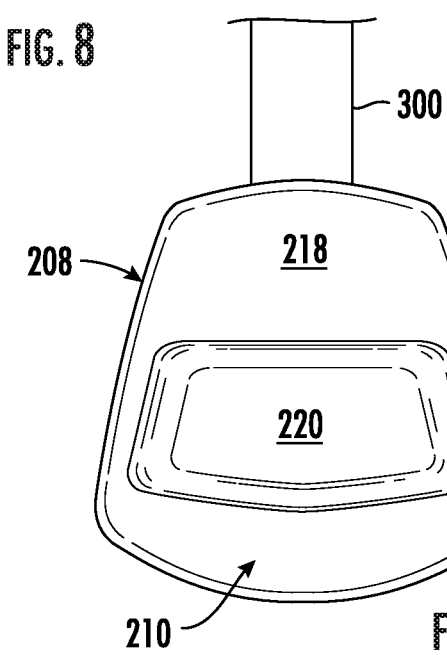
FIG. 9 is an anterior close-up view of the heel section with the upper foot plate removed.

The heel member 208 is substantially cup-shaped. An exterior surface 216 of the heel member 208 is curved and rounded to mimic the shape of a human heel or the shape of the shoe heel 204. As best seen in FIG. 9 with the upper foot plate 212 not shown, an interior surface 218 of the heel member 208 includes a recessed region 220 beneath the location of the connection point 214. The purpose of the recessed region 220 is to impart flexibility in the heel member 208 allowing it to flex slightly in the anterior to posterior direction, which allows the foot to move though partially through dorsiflexion and plantar flexion. The lower foot plate 210 may be curved between the heel end 222 and toe end 224 to such a degree that its curvature general coincides with the curvature of the shoe sole 207 between the shoe heel 204 and shoe toe 206. As illustrated in FIG. 7 with the shoe position and form indicated by dashed lines.

The heel member 208 is connected to or integrally constructed (monolithic) with the lower foot plate 210. The lower foot plate 210 extends longitudinally from a heel end 222 to a toe end 224 thereof. The longitudinal length of the lower foot plate 201 from the heel end 222 to the toe end 224 approximates the length of the wearer's foot or the shoe sole 202. The lateral width of the foot plate 210 approximates the width of the wearer's foot or the width of the shoe sole 202.

The upper foot plate 212 is positioned above the lower foot plate 210 at a distance D. The upper foot plate 212 may be connected to the lower foot plate 210 with at least one rigid mechanical link 226, which may be a hollow cylinder or the like through which a threaded fastener 228 fits. or another type of rigid mechanical link. In other examples, the rigid mechanical link may be integrally constructed with or adhered to the lower foot plate 210 and/or the upper foot plate 212. The purpose of the rigid mechanical link 226 is to provide a rigid mechanical link between the lower foot plate 210 and upper foot plate 212.

The upper foot plate 212 extends longitudinally from a heel end 230 to a toe end 232 thereof. The longitudinal length of the upper foot plate 212 from the heel end 230 to the toe end 232 approximates the length of the wearer's foot or the foot bed 234 of the shoe. The lateral width of the upper foot plate 212 approximates the width of the wearer's foot or the width of the foot bed 234 so that the bottom of the wearer's foot can completely rest on the upper foot plate 212.

In certain particular examples, the foot member 200 includes a shoe 202 such that the lower foot plate 210 and upper foot plate 212 are integrated into the shoe and not removable from the shoe 202 without destroying the shoe 202. As shown in the example of FIGS. 1-5, the upper foot plate 212 and lower foot plate 210 are not visible from the shoe's 202 exterior.

Figure 6:
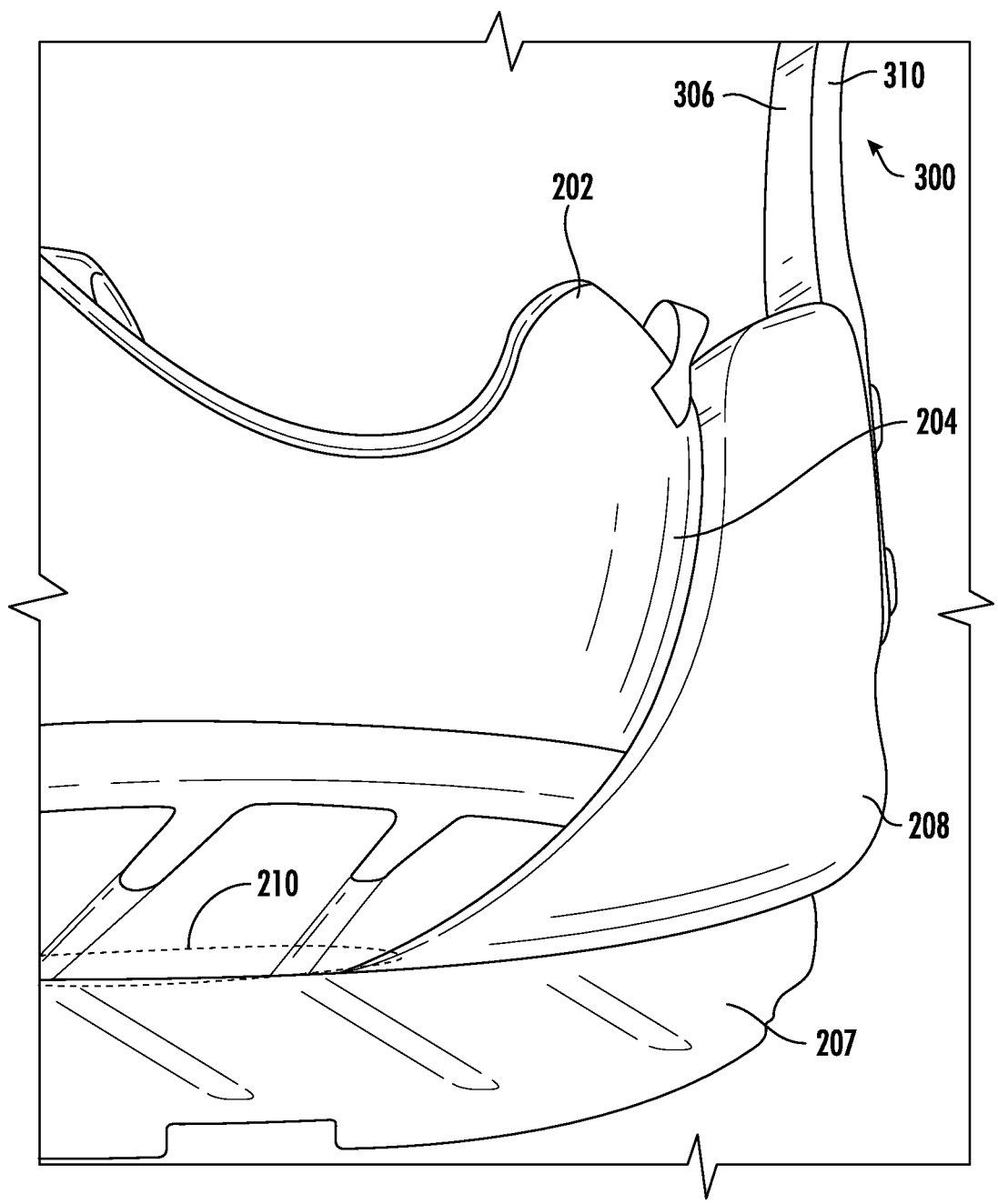
FIG. 6 is a partial view of the orthotic apparatus showing a close-up view of the heel member
Figure 10:
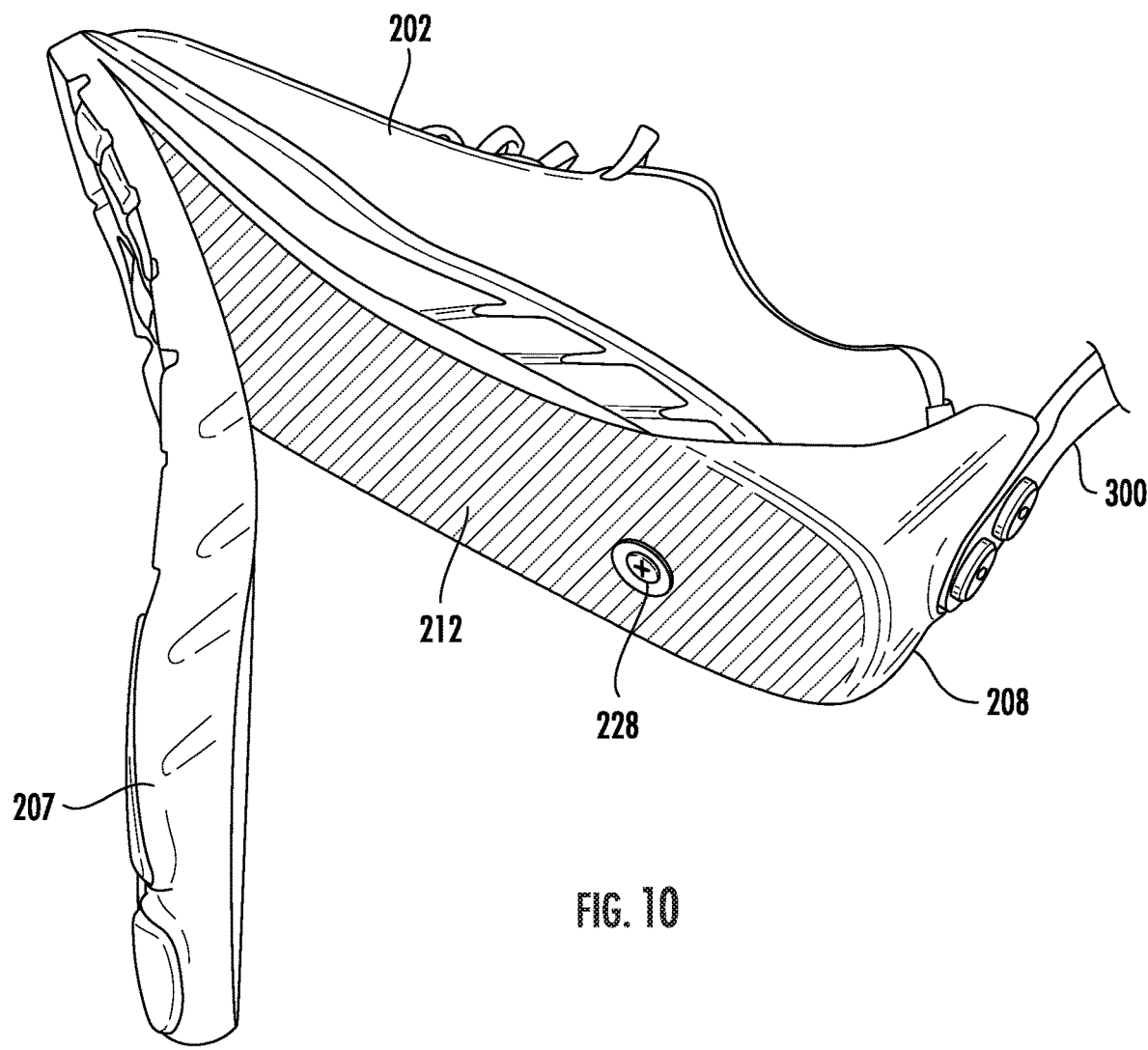
FIG. 10 is a bottom view of the shoe with the sole partially removed to reveal the lower foot plate therein.

The lower foot plate 210 is integrated into the shoe sole 207 as illustrated in FIG. 6, which shows the lower foot plate 210 (not visible but indicated with dashed lines) extending from the heel member 208 into the sole 207. As shown in FIG. 10, the lower foot plate 210 effectively bisects sole 207 into two sections.

Figure 11:
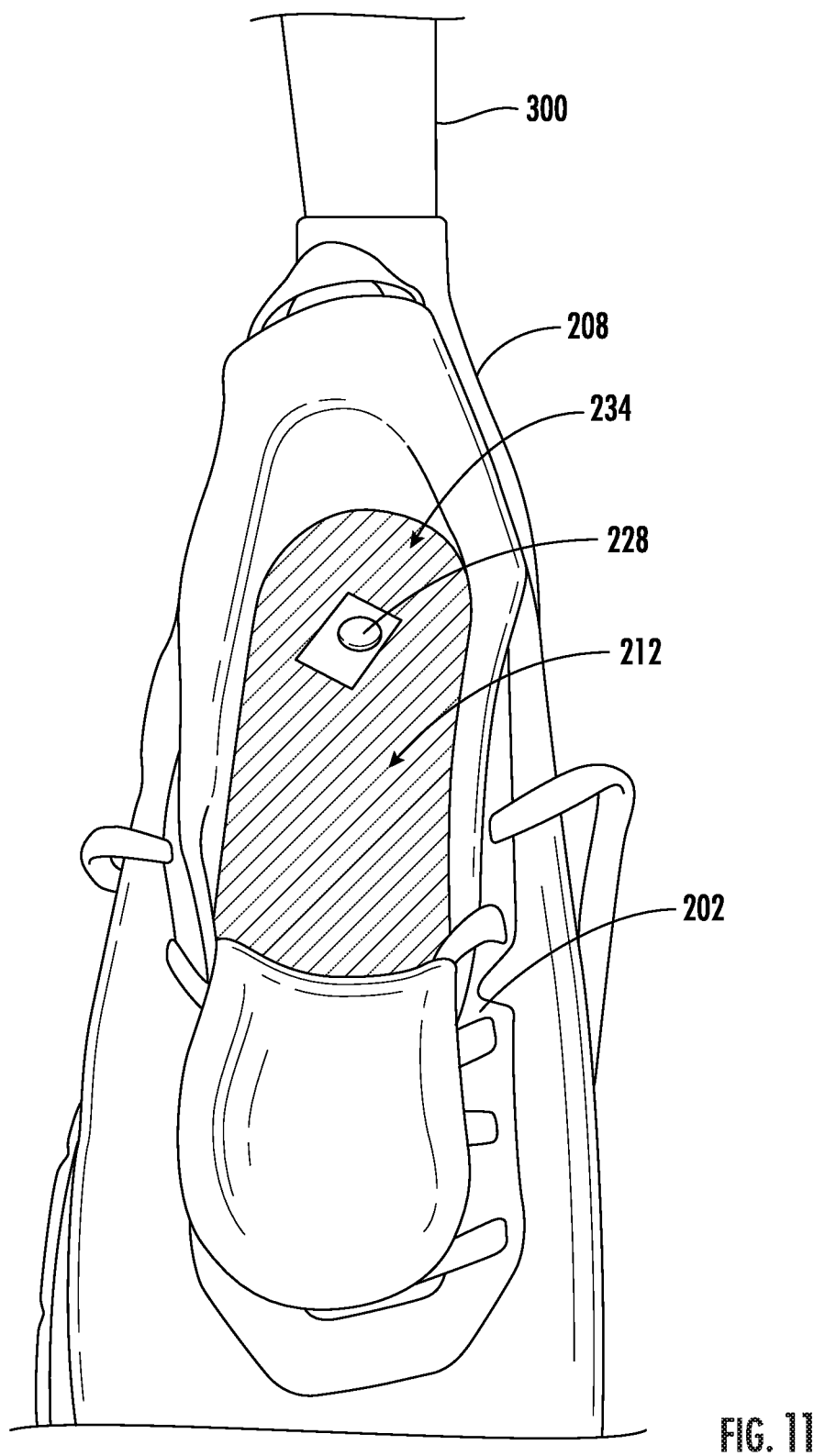
FIG. 11 is a top view of the shoe showing the upper foot plate in the foot bed.

Referring to FIG. 11, the upper foot plate 212 is positioned on the foot bed 234 of the shoe 202 to cradle the wearer's foot when the shoe 202 is worn. The upper foot plate 212 may be inserted into the foot bed 234 separately from the lower foot plate 210 and then attached to the lower foot plate 210 with a threaded fastener 228 or the like. In this example, the upper foot member 210 has a concave upper surface to comfortably cradle the foot.

The heel member 208, lower foot plate 210, and upper foot plate 212 may be made of a rigid resilient material such as a plastic or fabric reinforced polymer composite material such as carbon fiber or the like. A fabric reinforced polymer composite such as carbon fiber may be advantageous in many examples because it is rigid but can flex to store and release energy in a spring-like manner. This construction may help the foot member store and release energy as it flexes when the wearer walks, runs, or jumps. The upper foot plate 212 distributes the forces from the wearer's foot into the sole 207 and lower foot plate 210. The heel member 208 undergoes slight dorsiflexion and plantar flexion when the wearer tries to bend the ankle. The forces from these movements are transferred to the strut 300, which is slightly flexible in the anterior to posterior direction. And the strut 300 is anchored to the leg by the leg securing member 400.

As best seen in FIG. 6, the heel member 208 may partially extend around the shoe heel 204 if desired. This construction provides additional lateral support to the shoe heel 204 to prevent the shoe 202 from sliding laterally to a significant degree.

In other examples, the heel member 208 may be integrated into the shoe heel 204 so that the heel member 208 is not readily visible.

The leg securing member 400, strut 300, heel member 208, and lower foot plate 210 may be constructed, if desired, as an integrated single piece of material without any visible connectors or connections between them. In some case, the upper foot plate 212 may also be formed into the same single piece of material.

The various components of the foot member 200, the strut 300, and the leg securing member 400 may be constructed using conventional techniques. Where the material used is fabric reinforced polymer, the components may be molded into the desired size and shape. The heel member 208, lower foot plate 210, and upper foot plate 212 may, for example, be constructed using a mold corresponding to the shape of the shoe 202 with which they are to be combined.

By positioning the foot above the lower foot plate 210 on the upper foot plate 212, the wearer is able to apply more force associated with plantar flexion and dorsiflexion of the ankle to the strut 300 and heel member 208.

The apparatus may be used to treat any condition traditionally treated with an ankle foot orthotic, but is advantageously designed to provide improved planar flexion and dorsiflexion to the wearer. This allows the wearer to have greater rotation about the ankle than traditional AFOs, which is important when the wearer suffers from hip pain and/or back pain. The orthotic apparatus permits ankle flexion but provides enough lower leg support to alleviate the hip and/or back pain.

Accordingly, another aspect is a method of treating back and/or hip pain while walking. The method includes wearing the orthotic apparatus by attaching the leg securing member to the wearer's lower leg beneath the knee and resting the wearer's foot atop the upper foot plate while the wearer walks. This method advantageously improves ambulation of back and/or hip pain sufferers using an AFO-like orthotic device, but while still allowing plantar flexion and dorsiflexion about the ankle.

The term "connected to" is used in the claims to define a connection between two or more components. The use of this term is not intended to limit the scope of possible connection mechanisms. For example where a component is recited as being connected to another component, the connection mechanism may be a connection mechanism specified above or a different connection mechanism such as when the two components are integrated in monolithic construction.

The apparatus is not limited to the details described in connection with the example embodiments. There are numerous variations and modifications of the apparatus and methods that may be made without departing from the scope of what is claimed.

That which claimed is:

1. An orthotic apparatus having an anterior and posterior, the orthotic apparatus comprising:
    a leg securing member adapted for attachment to a wearer's lower leg;
    a resilient strut that flexes in the anterior to posterior direction, the resilient strut having a strut upper end and a strut lower end, the strut upper end being connected to the leg securing member;
    a heel member connected to the strut lower end;
    a foot member connected to the heel member, the foot member having a heel end at the heel member and a toe end spaced horizontally from the heel end, the foot member including (a) a substantially rigid lower foot plate extending between the heel end and toe end and (b) a substantially rigid upper foot plate extending between the heel end and toe end above and generally parallel to the substantially rigid lower foot plate; and
    a shoe, wherein the substantially rigid lower foot plate is positioned within a sole of the shoe and the substantially rigid upper foot plate is positioned on a foot bed of the shoe.

2. A method of treating back and/or hip pain while walking, the method comprising wearing the orthotic apparatus of claim 1 by attaching the leg securing member to the wearer's lower leg beneath the knee and resting the wearer's foot atop the substantially rigid upper foot plate while the wearer walks.

3. The orthotic apparatus of claim 1, wherein the resilient strut, substantially rigid upper foot plate, and substantially rigid lower foot plate are composed of resilient fiber-reinforced composite material.

4. The orthotic apparatus of claim 1, wherein the substantially rigid lower foot plate and heel member are monolithic and the substantially rigid upper foot plate is connected to the substantially rigid lower foot plate by rigid mechanical link between the substantially rigid upper foot plate and substantially rigid lower foot plate.

5. The orthotic apparatus of claim 1, wherein the substantially rigid upper foot plate is not in direct contact with the heel member.

6. The orthotic apparatus of claim 1, wherein the heel member is substantially cup-shaped and includes a recessed region that allows the heel member to flex in the anterior to posterior direction.

7. The orthotic apparatus of claim 1, wherein:
    the substantially rigid upper foot plate is a flattened plate configured to emulate a silhouette of wearer's foot in such a way that a bottom of the wearer's foot is configured to rest completely on the substantially rigid upper foot plate;
    the substantially rigid lower foot plate is a flattened plate extending from the heel end towards the toe end at least the same distance as the substantially rigid upper foot plate; and
    the substantially rigid upper foot plate is connected to the substantially rigid lower foot plate by a plurality of rigid mechanical links between the substantially rigid upper foot plate and substantially rigid lower foot plate, a first of the rigid mechanical links being towards the heel end and a second of the rigid mechanical links being towards the toe end, wherein the rigid mechanical links extend vertically from the substantially rigid lower foot plate to the substantially rigid upper foot plate.

8. The method of claim 2, wherein the resilient strut, substantially rigid upper foot plate, and substantially rigid lower foot plate are composed of resilient fiber-reinforced composite material.

9. The method of claim 2, wherein the substantially rigid lower foot plate and heel member are monolithic and the substantially rigid upper foot plate is connected to the substantially rigid lower foot plate by rigid mechanical link between the substantially rigid upper foot plate and substantially rigid lower foot plate.

10. The method of claim 2, wherein the substantially rigid upper foot plate is not in direct contact with the heel member.

11. The method of claim 2, wherein the heel member is substantially cup-shaped and includes a recessed region that allows the heel member to flex in the anterior to posterior direction.

12. The method of claim 2, wherein:
    the substantially rigid upper foot plate is a flattened plate configured to emulate a silhouette of wearer's foot in such a way that a bottom of the wearer's foot is configured to rest completely on the substantially rigid upper foot plate;
    the substantially rigid lower foot plate is a flattened plate extending from the heel end towards the toe end at least the same distance as the substantially rigid upper foot plate; and
    the substantially rigid upper foot plate is connected to the substantially rigid lower foot plate by a plurality of rigid mechanical links between the substantially rigid upper foot plate and substantially rigid lower foot plate, a first of the rigid mechanical links being towards the heel end and a second of the rigid mechanical links being towards the toe end, wherein the rigid mechanical links extend vertically from the substantially rigid lower foot plate to the substantially rigid upper foot plate.

13. An orthotic apparatus having an anterior and a posterior, the orthotic apparatus comprising:
    a shoe having a shoe heel end, a shoe toe end, and a sole;
    a foot member having a lower foot plate within the sole and an upper foot plate forming a foot bed of the shoe, the lower foot plate and upper foot plate extending from the shoe heel end toward the shoe toe end;

a heel member at the shoe heel end and connected to the lower foot plate;

a lower end of a resilient strut connected to the heel member and extending vertically; and a leg securing member for securing to a wearer's lower leg, the leg securing member being connected to an upper end of the resilient strut;

wherein the lower foot plate and heel member are monolithic and the upper foot plate is connected to the lower foot plate by rigid mechanical link between the upper foot plate and lower foot plate.

14. The orthotic apparatus of claim 13, wherein the resilient strut, upper foot plate, and lower foot plate are composed of resilient fiber-reinforced composite material.

15. The orthotic apparatus of claim 13, wherein the upper foot plate is not in direct contact with the heel member.

16. The orthotic apparatus of claim 13, wherein the heel member is substantially cup-shaped and includes a recessed surface that allows the heel member to flex in the anterior to posterior direction, thereby permitting plantar flexion and dorsiflexion of the foot member.

17. The orthotic apparatus of claim 13, wherein:

the upper foot plate is a flattened plate configured to emulate a silhouette of wearer's foot in such a way that a bottom of the wearer's foot is configured to rest completely on the upper foot plate;

the lower foot plate is a flattened plate extending from the shoe heel end towards the shoe toe end at least the same distance as the upper foot plate; and the upper foot plate is connected to the lower foot plate by a plurality of rigid mechanical links between the upper foot plate and lower foot plate, a first of the rigid mechanical links being towards the shoe heel end and a second of the rigid mechanical links being towards the shoe toe end, wherein the rigid mechanical links extend vertically from the lower foot plate to the upper foot plate through the sole.

18. An orthotic apparatus having an anterior and posterior, the orthotic apparatus comprising:

a leg securing member adapted for attachment to a wearer's lower leg;

a resilient strut that flexes in the anterior to posterior direction, the resilient strut having a strut upper end and a strut lower end, the strut upper end being connected to the leg securing member;

a heel member connected to the strut lower end; and a foot member connected to the heel member, the foot member having a heel end at the heel member and a toe end spaced horizontally from the heel end, the foot member including (a) a substantially rigid lower foot plate extending between the heel end and toe end and (b) a substantially rigid upper foot plate extending between the heel end and toe end above and generally parallel to the substantially rigid lower foot plate;

wherein the substantially rigid lower foot plate and heel member are monolithic and the substantially rigid upper foot plate is connected to the substantially rigid lower foot plate by at least one rigid mechanical link between the substantially rigid upper foot plate and substantially rigid lower foot plate.

19. The orthotic apparatus of claim 18, wherein the substantially rigid upper foot plate is not in direct contact with the heel member.

20. The orthotic apparatus of claim 18, wherein the heel member is substantially cup-shaped and includes a recessed region that allows the heel member to flex in the anterior to posterior direction.

21. The orthotic apparatus of claim 18, wherein:

the substantially rigid upper foot plate is a flattened plate configured to emulate a silhouette of wearer's foot in such a way that a bottom of the wearer's foot is configured to rest completely on the substantially rigid upper foot plate;

the substantially rigid lower foot plate is a flattened plate extending from the heel end towards the toe end at least the same distance as the substantially rigid upper foot plate; and the substantially rigid upper foot plate is connected to the substantially rigid lower foot plate by a plurality of the rigid mechanical links between the substantially rigid upper foot plate and substantially rigid lower foot plate, a first of the rigid mechanical links being towards the heel end and a second of the rigid mechanical links being towards the toe end, wherein the rigid mechanical links extend vertically from the substantially rigid lower foot plate to the substantially rigid upper foot plate.

22. The orthotic apparatus of claim 18, further comprising a shoe, wherein the substantially rigid lower foot plate is positioned within a sole of the shoe and the substantially rigid upper foot plate is positioned on a foot bed of the shoe.

23. The orthotic apparatus of claim 18, wherein the resilient strut, substantially rigid upper foot plate, and substantially rigid lower foot plate are composed of resilient fiber-reinforced composite material.

24. An orthotic apparatus having an anterior and a posterior, the orthotic apparatus comprising:

a shoe having a shoe heel end, a shoe toe end, and a sole;

a foot member having a lower foot plate within the sole and an upper foot plate forming a foot bed of the shoe, the lower foot plate and upper foot plate extending from the shoe heel end toward the shoe toe end;

a heel member at the shoe heel end and connected to the lower foot plate;

a lower end of a resilient strut connected to the heel member and extending vertically; and a leg securing member for securing to a wearer's lower leg, the leg securing member being connected to an upper end of the resilient strut;

wherein the upper foot plate is not in direct contact with the heel member.

25. The orthotic apparatus of claim 24, wherein the lower foot plate and heel member are monolithic and the upper foot plate is connected to the lower foot plate by a rigid mechanical link between the upper foot plate and lower foot plate.

26. The orthotic apparatus of claim 24, wherein the heel member is substantially cup-shaped and includes a recessed surface that allows the heel member to flex in the anterior to posterior direction, thereby permitting plantar flexion and dorsiflexion of the foot member.

27. The orthotic apparatus of claim 24, wherein:

the upper foot plate is a flattened plate configured to emulate a silhouette of wearer's foot in such a way that a bottom of the wearer's foot is configured to rest completely on the upper foot plate;

the lower foot plate is a flattened plate extending from the shoe heel end towards the shoe toe end at least the same distance as the upper foot plate; and the upper foot plate is connected to the lower foot plate by a plurality of rigid mechanical links between the upper foot plate and lower foot plate, a first of the rigid mechanical links being towards the shoe heel end and a second of the rigid mechanical links being towards the shoe toe end, wherein the rigid mechanical links extend vertically from the lower foot plate to the upper foot plate through the sole.

28. The orthotic apparatus of claim 24, wherein the resilient strut, upper foot plate, and lower foot plate are composed of resilient fiber-reinforced composite material.

29. A method of treating back and/or hip pain while walking, the method comprising wearing the orthotic apparatus of claim 18 by attaching the leg securing member to the wearer's lower leg beneath the knee and resting the wearer's foot atop the substantially rigid upper foot plate while the wearer walks.

30. The method of claim 29, wherein the substantially rigid upper foot plate is not in direct contact with the heel member.

31. The method of claim 29, wherein the heel member is substantially cup-shaped and includes a recessed region that allows the heel member to flex in the anterior to posterior direction.

32. The method of claim 29, wherein:
the substantially rigid upper foot plate is a flattened plate configured to emulate a silhouette of wearer's foot in such a way that a bottom of the wearer's foot is configured to rest completely on the substantially rigid upper foot plate;
the substantially rigid lower foot plate is a flattened plate extending from the heel end towards the toe end at least the same distance as the substantially rigid upper foot plate; and
the substantially rigid upper foot plate is connected to the substantially rigid lower foot plate by a plurality of the rigid mechanical links between the substantially rigid upper foot plate and substantially rigid lower foot plate, a first of the rigid mechanical links being towards the heel end and a second of the rigid mechanical links being towards the toe end, wherein the rigid mechanical links extend vertically from the substantially rigid lower foot plate to the substantially rigid upper foot plate.

33. The method of claim 29, further comprising a shoe, wherein the substantially rigid lower foot plate is positioned within a sole of the shoe and the substantially rigid upper foot plate is positioned on a foot bed of the shoe.

34. The method of claim 29, wherein the resilient strut, substantially rigid upper foot plate, and substantially rigid lower foot plate are composed of resilient fiber-reinforced composite material.

35. An orthotic apparatus having an anterior and posterior, the orthotic apparatus comprising:
a leg securing member adapted for attachment to a wearer's lower leg;
a resilient strut that flexes in the anterior to posterior direction, the resilient strut having a strut upper end and a strut lower end, the strut upper end being connected to the leg securing member;
a heel member connected to the strut lower end;
a foot member connected to the heel member, the foot member having a heel end at the heel member and a toe end spaced horizontally from the heel end, the foot member including (a) a substantially rigid lower foot plate extending between the heel end and toe end and (b) a substantially rigid upper foot plate extending between the heel end and toe end above and generally parallel to the substantially rigid lower foot plate; and
wherein the substantially rigid upper foot plate is not in direct contact with the heel member.

36. The orthotic apparatus of claim 35, wherein the substantially rigid lower foot plate and heel member are monolithic and the substantially rigid upper foot plate is connected to the substantially rigid lower foot plate by a rigid mechanical link between the substantially rigid upper foot plate and substantially rigid lower foot plate.

37. The orthotic apparatus of claim 35, wherein the heel member is substantially cup-shaped and includes a recessed region that allows the heel member to flex in the anterior to posterior direction.

38. The orthotic apparatus of claim 35, wherein:
the substantially rigid upper foot plate is a flattened plate configured to emulate a silhouette of wearer's foot in such a way that a bottom of the wearer's foot is configured to rest completely on the substantially rigid upper foot plate;
the substantially rigid lower foot plate is a flattened plate extending from the heel end towards the toe end at least the same distance as the substantially rigid upper foot plate; and
the substantially rigid upper foot plate is connected to the substantially rigid lower foot plate by a plurality of rigid mechanical links between the substantially rigid upper foot plate and substantially rigid lower foot plate, a first of the rigid mechanical links being towards the heel end and a second of the rigid mechanical links being towards the toe end, wherein the rigid mechanical links extend vertically from the substantially rigid lower foot plate to the substantially rigid upper foot plate.

39. The orthotic apparatus of claim 35, further comprising a shoe, wherein the substantially rigid lower foot plate is positioned within a sole of the shoe and the substantially rigid upper foot plate is positioned on a foot bed of the shoe.

40. The orthotic apparatus of claim 35, wherein the resilient strut, substantially rigid upper foot plate, and substantially rigid lower foot plate are composed of resilient fiber-reinforced composite material.

41. A method of treating back and/or hip pain while walking, the method comprising wearing the orthotic apparatus of claim 35 by attaching the leg securing member to the wearer's lower leg beneath the knee and resting the wearer's foot atop the substantially rigid upper foot plate while the wearer walks.

42. The method of claim 41, wherein the substantially rigid lower foot plate and heel member are monolithic and the substantially rigid upper foot plate is connected to the substantially rigid lower foot plate by a rigid mechanical link between the substantially rigid upper foot plate and substantially rigid lower foot plate.

43. The method of claim 41, wherein the heel member is substantially cup-shaped and includes a recessed region that allows the heel member to flex in the anterior to posterior direction.

44. The method of claim 41, wherein:
the substantially rigid upper foot plate is a flattened plate configured to emulate a silhouette of wearer's foot in such a way that a bottom of the wearer's foot is configured to rest completely on the substantially rigid upper foot plate;

the substantially rigid lower foot plate is a flattened plate extending from the heel end towards the toe end at least the same distance as the substantially rigid upper foot plate; and the substantially rigid upper foot plate is connected to the substantially rigid lower foot plate by a plurality of rigid mechanical links between the substantially rigid upper foot plate and substantially rigid lower foot plate, a first of the rigid mechanical links being towards the heel end and a second of the rigid mechanical links being towards the toe end, wherein the rigid mechanical links extend vertically from the substantially rigid lower foot plate to the substantially rigid upper foot plate.

45. The method of claim 41, further comprising a shoe, wherein the substantially rigid lower foot plate is positioned within a sole of the shoe and the substantially rigid upper foot plate is positioned on a foot bed of the shoe.

46. The method of claim 41, wherein the resilient strut, substantially rigid upper foot plate, and substantially rigid lower foot plate are composed of resilient fiber-reinforced composite material.

47. An orthotic apparatus having an anterior and posterior, the orthotic apparatus comprising:
a leg securing member adapted for attachment to a wearer's lower leg;
a resilient strut that flexes in the anterior to posterior direction, the resilient strut having a strut upper end and a strut lower end, the strut upper end being connected to the leg securing member;
a heel member connected to the strut lower end;
a foot member connected to the heel member, the foot member having a heel end at the heel member and a toe end spaced horizontally from the heel end, the foot member including (a) a substantially rigid lower foot plate extending between the heel end and toe end and (b) a substantially rigid upper foot plate extending between the heel end and toe end above and generally parallel to the substantially rigid lower foot plate; and
wherein:
the substantially rigid upper foot plate is a flattened plate configured to emulate a silhouette of wearer's foot in such a way that a bottom of the wearer's foot is configured to rest completely on the substantially rigid upper foot plate;
the substantially rigid lower foot plate is a flattened plate extending from the heel end towards the toe end at least the same distance as the substantially rigid upper foot plate; and
the substantially rigid upper foot plate is connected to the substantially rigid lower foot plate by a plurality of rigid mechanical links between the substantially rigid upper foot plate and substantially rigid lower foot plate, a first of the rigid mechanical links being towards the heel end and a second of the rigid mechanical links being towards the toe end, wherein the rigid mechanical links extend vertically from the substantially rigid lower foot plate to the substantially rigid upper foot plate.

48. The orthotic apparatus of claim 47, wherein the substantially rigid lower foot plate and heel member are monolithic and the substantially rigid upper foot plate is connected to the substantially rigid lower foot plate by the rigid mechanical links between the substantially rigid upper foot plate and substantially rigid lower foot plate.

49. The orthotic apparatus of claim 47, wherein the substantially rigid upper foot plate is not in direct contact with the heel member.

50. The orthotic apparatus of claim 47, wherein the heel member is substantially cup-shaped and includes a recessed region that allows the heel member to flex in the anterior to posterior direction.

51. The orthotic apparatus of claim 47, further comprising a shoe, wherein the substantially rigid lower foot plate is positioned within a sole of the shoe and the substantially rigid upper foot plate is positioned on a foot bed of the shoe.

52. The orthotic apparatus of claim 47, wherein the resilient strut, substantially rigid upper foot plate, and substantially rigid lower foot plate are composed of resilient fiber-reinforced composite material.

53. An orthotic apparatus having an anterior and a posterior, the orthotic apparatus comprising:
a shoe having a shoe heel end, a shoe toe end, and a sole;
a foot member having a lower foot plate within the sole and an upper foot plate forming a foot bed of the shoe, the lower foot plate and upper foot plate extending from the shoe heel end toward the shoe toe end;
a heel member at the shoe heel end and connected to the lower foot plate;
a lower end of a resilient strut connected to the heel member and extending vertically; and
a leg securing member for securing to a wearer's lower leg, the leg securing member being connected to an upper end of the resilient strut;
wherein:
the upper foot plate is a flattened plate configured to emulate a silhouette of wearer's foot in such a way that a bottom of the wearer's foot is configured to rest completely on the upper foot plate;
the lower foot plate is a flattened plate extending from the shoe heel end towards the shoe toe end at least the same distance as the upper foot plate; and
the upper foot plate is connected to the lower foot plate by a plurality of rigid mechanical links between the upper foot plate and lower foot plate, a first of the rigid mechanical links being towards the shoe heel end and a second of the rigid mechanical links being towards the shoe toe end, wherein the rigid mechanical links extend vertically from the lower foot plate to the upper foot plate through the sole.

54. The orthotic apparatus of claim 53, wherein the lower foot plate and heel member are monolithic and the upper foot plate is connected to the lower foot plate by the rigid mechanical links between the upper foot plate and lower foot plate.

55. The orthotic apparatus of claim 53, wherein the upper foot plate is not in direct contact with the heel member.

56. The orthotic apparatus of claim 53, wherein the heel member is substantially cup-shaped and includes a recessed surface that allows the heel member to flex in the anterior to posterior direction, thereby permitting plantar flexion and dorsiflexion of the foot member.

57. The orthotic apparatus of claim 53, wherein the resilient strut, upper foot plate, and lower foot plate are composed of resilient fiber-reinforced composite material.

58. A method of treating back and/or hip pain while walking, the method comprising wearing the orthotic apparatus of claim 47 by attaching the leg securing member to the wearer's lower leg beneath the knee and resting the wearer's foot atop the substantially rigid upper foot plate while the wearer walks.

59. The method of claim 58, wherein the substantially rigid lower foot plate and heel member are monolithic and the substantially rigid upper foot plate is connected to the substantially rigid lower foot plate by the rigid mechanical links between the substantially rigid upper foot plate and substantially rigid lower foot plate.

60. The method of claim 58, wherein the substantially rigid upper foot plate is not in direct contact with the heel member.

61. The method of claim 58, wherein the heel member is substantially cup-shaped and includes a recessed region that allows the heel member to flex in the anterior to posterior direction.

62. The method of claim 58, further comprising a shoe, wherein the substantially rigid lower foot plate is positioned within a sole of the shoe and the substantially rigid upper foot plate is positioned on a foot bed of the shoe.

63. The method of claim 58, wherein the resilient strut, substantially rigid upper foot plate, and substantially rigid lower foot plate are composed of resilient fiber-reinforced composite material.

\* \* \* \* \*